US00RE49443E

(19) United States
(12) Reissued Patent
Mitidieri et al.

(10) Patent Number: US RE49,443 E
(45) **Date of Reissued Patent: *Mar. 7, 2023**

(54) PROCESS FOR PRODUCING A STABLE LOW CONCENTRATION, INJECTABLE SOLUTION OF NORADRENALINE

(71) Applicant: Sintetica S.A., Mendrisio (CH)

(72) Inventors: Augusto Mitidieri, Lugano (CH); Elisabetta Donati, Cavallasca (IT); Nicola Caronzolo, Bissone (CH)

(73) Assignee: Sintetica S.A., Mendrisio (CH)

( * ) Notice: This patent is subject to a terminal disclaimer.

(21) Appl. No.: 17/006,838

(22) Filed: Aug. 30, 2020

Related U.S. Patent Documents

Reissue of:
(64) Patent No.: 10,251,848
Issued: Apr. 9, 2019
Appl. No.: 15/118,864
PCT Filed: Feb. 26, 2015
PCT No.: PCT/EP2015/054021
§ 371 (c)(1),
(2) Date: Aug. 13, 2016
PCT Pub. No.: WO2015/128418
PCT Pub. Date: Sep. 3, 2015

(30) Foreign Application Priority Data

Feb. 27, 2014 (IT) ..... MI2014A000306

(51) Int. Cl.
*A61K 31/137* (2006.01)
*A61K 9/00* (2006.01)
*A61K 9/08* (2006.01)
*A61K 47/02* (2006.01)
*A61L 2/00* (2006.01)

(52) U.S. Cl.
CPC ..... *A61K 31/137* (2013.01); *A61K 9/0019* (2013.01); *A61K 9/08* (2013.01); *A61K 47/02* (2013.01); *A61L 2/0023* (2013.01)

(58) Field of Classification Search
CPC ..... A61K 31/137
See application file for complete search history.

(56) References Cited

U.S. PATENT DOCUMENTS

| | | | | |
|---|---|---|---|---|
| 10,251,848 | B2 | 4/2019 | Mitidieri | |
| 2004/0005401 | A1 | 3/2004 | Dietlin | |
| 2004/0054012 | A1 | 3/2004 | Dietlin | |
| 2005/0007061 | A1 | 3/2005 | Dinnequin | |
| 2005/0070613 | A1* | 3/2005 | Dinnequin | A61K 31/137 514/734 |
| 2009/0004470 | A1 | 2/2009 | Dietlin | |
| 2009/0044700 | A1 | 2/2009 | Dietlin et al. | |
| 2011/0000301 | A1 | 1/2011 | Baillie | |
| 2011/0003015 | A1 | 1/2011 | Baillie et al. | |
| 2012/0129944 | A1* | 5/2012 | Baillie | A61P 9/02 564/361 |
| 2013/0123298 | A1 | 5/2013 | Julia | |
| 2016/0005871 | A1 | 3/2016 | Rakesh | |

FOREIGN PATENT DOCUMENTS

| | | | |
|---|---|---|---|
| CN | 102525895 | B | 1/2020 |
| WO | 2004000219 | A2 | 12/2003 |
| WO | 2010139752 | A1 | 9/2010 |
| WO | 2015128418 | A1 | 9/2015 |
| WO | 2018140894 | A1 | 8/2018 |

OTHER PUBLICATIONS

Maik W. Jornitz The role of sterile filtration in the biopharm industry. Pharmaceutical Technology Europe—Jan. 7, 2011, vol. 23, Issue 1 (Year: 2011).*

Tremblay et al. Stability of norepinephrine infusions prepared in dextrose and normal saline solutions. Can J Anesth 2008 55: 3 pp. 163-167 (Year: 2008).*

Polypropylene Aceso PPM R020 S01 Technical Data Sheet, Total Research and Technology Feluy, Jul. 2015.

ASTM D1003—13 Standard Test Method for Haze and Luminous Transmittance of Transparent Plastics, Oct. 15, 2020.

Multilayer Flexible Packaging Chapter 3, Polypropylene, Allison Calhoun, 2009.

Public Assessment Report Decentralised Procedure Noradrenaline Sintetica 1 mg/ml Konzentrat zur Herstellung einer Infusionslösung; Noradrenaline Sintetica 0,1 mg/ml; 0,2 mg/ml Infusionslösung; Procedure No. DE/H/5453/01-03/DC, Apr. 7, 2020.

Film Properties of Plastics and Elastomers (Third Edition) Plastics Design Library 2012, pp. 219-254, Film Properties of Plastics and Elastomers 10—Polyvinyls and Acrylics, Laurence W.McKeen.

The Science and Technology of Flexible Packaging, Multilayer Films from Resin and Process to End Use, Plastics Design Library 2017, pp. 69-119, Chapter 4—Commonly Used Resins and Substrates in Flexible Packaging, Barry A. Morris.

Guidance for Industry Q1B Photostability Testing of New Drug Substances and Products, ICH 1996.

English Translation of a Colombian Office Action dated Feb. 2, 2018 in a counterpart patent application.

Norepinephrine Bitartrate—norepinephrine bitartrate injection Baxter Healthcare Corporation (dated Oct. 31, 2018).

Noradrenaline (Norepinephrine) 1 mg/ml Concentrate for Solution for Infusion Summary of Product Characteristics, Hospira UK Ltd. (dated May 14, 2018).

(Continued)

*Primary Examiner* — Bruce R Campell
(74) *Attorney, Agent, or Firm* — Clark G. Sullivan

(57) ABSTRACT

In a first aspect, the present invention relates to a process for producing a stable, injectable solution with low content of noradrenaline, which includes dissolving noradrenaline and optionally an excipient in deoxygenated or degassed water, filtrating the resulting noradrenaline solution in a nitrogen current, distributing the solution in a nitrogen current, and sterilization, preferably hot. The invention further provides a stable, injectable solution with low content of noradrenaline, substantially free of anti-oxidizing and preservative agents, as well as uses thereof in the medical and pharmaceutical fields.

25 Claims, No Drawings

(56) References Cited

OTHER PUBLICATIONS

Sintetica Study Report Diluted Adrenaline (dated Nov. 13, 2015).
Bathochromic Shift, Wikipedia, dated Jan. 18, 2019.
Sintetica Study Report Diluted Adrenaline Addendum 3, dated Sep. 12, 2019.
Expert Declaration, Alain Borgeat, dated Apr. 21, 2020.
Sintetica Study Report Diluted Adrenaline Addendum 4, dated Apr. 26, 2020.
Written Decision in counterpart European application EP15712064.3 dated Dec. 19, 2019.
Sintetica Appeal Brief in counterpart European application EP15712064.3, dated Apr. 29, 2020.
Gilliot et al., Long-term stability of ready-to-use norepinephrine solution at 0.2 and 0.5 mg/mL. Eur J Hosp Pharm 2020;27:e93-e98.
Heeb et al.: Stability of Epinephrine and Norepinephrine Solutions. Pharm. Technol. Hosp. Pharm. 2017; 2(4): 159-171.
Hollein et al., Ficts and facts of epinephrine and norepinephrine stability in injectable solutions. Internationa!Journal of Pharmaceutics 434 (2012) 468-480.
Levophed® Norepinephrine Bitartrate Injection, USP. Hospira Inc., dated Jun. 2007.
Mylan Group, High Barrier Co-Extrusion Film—PP/Tie/EVOH/Tie/PP. dated Jul. 9, 2020.
Stepensky et al., Long-Term Stability Study of L-Adrenaline Injections: Kinetics of Sulfonation and Racemization Pathways of Drug Degradation. Journal of Pharmaceutical Sciences, vol. 93, No. 4, Apr. 2004.
Tremblay et al., Stability of norepinephrine infusions prepared in dextrose and normal saline solutions. Can J Anesth 55: Mar. 3, 2008.
United States Pharmacopoeia Chapter□788□Particulate Matter in Injections, Dated May 1, 2013.
Tran et al., Quality Control Analytical Methods: Particulate Matter in Injections: What is it and what are the concerns? International Journal of Pharmaceutical Compounding, vol. 10 No. 3 May/Jun. 2006.
Walker et al., Stability of Norepinephrine Solutions in Normal Saline and 5% Dextrose in Water. Can J Hosp Pharm 2010;63(2):113-118.
Search Report and Written Opinion of PCT/EP2015/054021 dated May 8, 2015.
Parry, T., et al., "Physical and chemical considerations in the in vitro calibration of microdyalisis probes for biogenic amine neurotransmitters and metabolites," Journal of Neuroscience Methods, Elsevier Science Publisher, B.V. Amsterdam, NL, vol. 32, No. 3, Jun. 1, 1990, pp. 175-183.
International Preliminary Report on Patentability of PCT/EP2015/054021 dated Apr. 28, 2016.
Original and English Translation of Office Action dated Sep. 4, 2018 in counterpart Japanese application No. JP 2016-551222.
Boomsma F., et al., "Optimal collection and storage conditions for catecholamine measurements in human plasma and urine", Clin. Chem. 39/12, 2503-2508 (1993).
Corona-Avendano S., et al., "Study on the stability of noradrenaline and on the determination of its acidity constants", Spectrochimica Acta Part A 61 (2005) 3139-3144.
Noradrenaline List of Updates.
Noradrenaline Screenshot of Medicines.
Notice of Opposition dated Oct. 16, 2018 in counterpart European application EP15712064.3.

* cited by examiner

PROCESS FOR PRODUCING A STABLE LOW CONCENTRATION, INJECTABLE SOLUTION OF NORADRENALINE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

[This application is a U.S. national stage of PCT/EP2015/054021 filed on 26 Feb. 2015, which claims priority to and the benefit of Italian Application No. MI2014A000306 filed on 27 Feb. 2014, the contents of which are incorporated herein by reference in their entireties.] *This application is an application for reissue of U.S. application Ser. No. 15/118,164, filed Feb. 26, 2015, entitled "Process for producing a stable low concentration, injectable solution of noradrenaline," granted as U.S. Pat. No. 10,251,848 on Apr. 9, 2019, which is a national stage entry of PCT/EP2015/054021, filed Feb. 26, 2015, which claims priority to MI2014A0306, filed Feb. 27, 2014. This application is co-pending with U.S. application Ser. Nos. 17/006,840 and 17/006,841, filed Aug. 30, 2020, both of which are also applications for reissue of U.S. application Ser. No. 15/118,164, filed Feb. 26, 2015, entitled "Process for producing a stable low concentration, injectable solution of noradrenaline," granted as U.S. Pat. No. 10,251,848 on Apr. 9, 2019.*

FIELD OF THE INVENTION

The present invention relates to a process for producing a stable low concentration, injectable solution of noradrenaline.

The present invention originates in the field of pharmaceutical technology and industrial processes for the production of active ingredients.

Specifically, the present invention relates to a process for producing an injectable solution containing noradrenaline at low concentration as active ingredient, and highly stable, injectable solutions of noradrenaline at low concentration, typically obtained with this process.

STATE OF THE ART

Noradrenaline or norepinephrine is a catecholamine or an amine compound with the structure similar to that of catechol and having the chemical formula $C_8H_{11}NO_3$. From a physiological standpoint, noradrenaline is a chemical mediator with sympathomimetic action on the transmission of nervous impulses at neuroeffector junctions of the sympathetic nervous system. Noradrenaline is released at the postganglionic ortho-sympathetic (or sympathetic) nerve endings and at adrenal medulla, and acts on both types of adrenergic receptors responsible for the action of sympathomimetics at the level of various effector organs, but with prevalence of alpha type actions.

From a pharmacological standpoint, noradrenaline performs many activities, mainly confined to the level of the circulatory apparatus. It causes arteriolar vasoconstriction with increased peripheral resistance and blood pressure. Noradrenaline has no particularly evident effects on the heart, but can cause, by reflex paths, a decrease of the heart rate through a vagal reflex. Noradrenaline also produces a moderate relaxation of bronchial smooth muscle and gastrointestinal muscle and modest action at the level of the central nervous system and the cerebral circle.

From a therapeutic point of view, it is used for its pressor effects in conditions of acute hypotension, particularly if accompanied by loss of peripheral vascular tone. Typically, the action of noradrenaline is short-lived, because this molecule is rapidly inactivated in the body through two metabolic pathways: oxidative deamination, operated by the oxidase, and methylation, operated by the methyltransferase.

Noradrenaline is commonly administered in the form of solution, by intravenous slow infusion, and finds application in the case of cardiovascular collapse, in states of shock associated with low peripheral resistance, the so-called septic shock, and to restore and maintain physiological blood pressure levels.

Noradrenaline solutions for injection, at a concentration of 1 mg/ml, are available on the market.

Noradrenaline, such as the catecholamines in general, has the drawback of being easily decomposable substances, when exposed to oxygen of the air. On contact with oxygen, noradrenaline decomposes giving quinone by-products, i.e. compounds which impart a strong coloration to the pharmaceutical solution, thus highlighting the denaturation of the active principle.

In the practice of pharmaceutical technology, this problem is at least partially obviated by adding anti-oxidizing agents and/or preservatives to the injectable noradrenaline solutions.

Sulfites are anti-oxidizing agents commonly used to stabilize injectable noradrenaline solutions. However, the use of sulfites is not without disadvantages, since their presence within the pharmaceutical formulations is associated with an increased risk of developing allergic or sensitization reactions.

Furthermore, sulfites in an aqueous solution tend to interact with adrenaline through addition reactions. These reactions are accelerated because of the exposure of the solution to heat, such as occurs in the treatment of high temperature sterilization of injectable solutions.

To overcome these problems, processes were adopted for the production of noradrenaline injectable solutions, which took advantage of high vacuum packaging technologies.

However, available technologies have not proven adequate, in particular when applied to processes in which the solution final sterilization step is performed at high temperature. In fact, these conditions increase the risks of deterioration of the active principle. Presence of oxygen or even of trace metals in the injectable solution is sufficient to denaturate noradrenaline contained in the aqueous solution.

Currently, there is a need for technologies for the production of injectable solutions of noradrenaline at low concentration for medical use, which are stable and simple to manufacture.

One of the objects of the present invention is to provide a process for producing an injectable solution of noradrenaline with low concentration of active ingredient, that is stable and provided with an improved compliance and safety profile for the patient.

A further object is to provide an injectable solution at low concentration of noradrenaline, that is highly stable and free of preserving agents or anti-oxidizing allergenic agents such as sulphites.

SUMMARY OF THE INVENTION

The Applicant has found that a noradrenaline solution for injection, particularly stable even in the absence of preservatives and anti-oxidizing, is obtained by adopting a combination of specific conditions in the field of pharmaceutical production technology.

According to a general aspect the invention relates to a process for producing a low concentration injectable noradrenaline solution which is highly stable in the absence of anti-oxidizing or preservative agents, as defined in any one of claims 1-8.

According to this first aspect there is provided a process for producing a low concentration injectable noradrenaline solution comprising the following steps:

a. dissolving noradrenaline and optionally an excipient in deoxygenated or degassed water,
b. adjusting the pH of the resulting solution by adding hydrochloric acid until a value in the range from 3.2-3.6 is achieved,
c. filtrating the resulting noradrenaline solution in an inert gas current,
d. distribution of the solution in a current of an inert gas,
e. sterilization of the solution.

In the process of the invention, the oxidation of noradrenaline is substantially prevented using degassed or deoxygenated water, typically by bubbling or blowing a stream of inert gas and performing the subsequent steps in substantial absence of air or oxygen, through the use of an inert gas.

The conditions previously reported, combined with acid values of pH of the noradrenaline solution, selected in the range from 3.2 to 3.6, in particular from 3.3 to 3.6, prevent or substantially reduce the occurrence of oxidation and/or racemization of noradrenaline, thus preventing its denaturation and the formation of dextrorotatory isomer, which has a reduced therapeutic activity.

The inventors found that, in the specific process conditions according to the invention, the noradrenaline solution obtained has a stability at least equal to that of an injectable solution of equal noradrenaline concentration added with sulphites, according to the prior art, while avoiding the risks associated with the use of preservatives.

Furthermore, Applicant found that racemization occurs at pH values lower than 3, while it is almost absent at the values selected according to the invention. Conversely, Applicant found that the incidence of oxidative phenomena that lead to the formation of the main degradation product, i.e. arterenone, increases at pH values higher than 4.

According to another aspect, the present invention provides a noradrenaline injectable solution that is stable, substantially free of preservatives, complexing agent and/or anti-oxidizing agent, as defined in any one of claims 9-16.

In certain embodiments of the invention noradrenaline is noradrenaline base or a pharmaceutically acceptable noradrenaline salt such as noradrenaline tartrate or bitartrate or bitartrate monohydrate.

According to some embodiments, the stable noradrenaline solution is obtained by the process described above.

According to some preferred embodiments, the injectable solution has a low concentration of noradrenaline, in the range of 0.04 mg/ml to 0.20 mg/ml.

According to a further aspect, a stable, injectable solution with a content of noradrenaline in the range of 0.04 mg/ml to 0.20 mg/ml is provided, for use in medicine, in particular for the treatment of cardiac circulatory collapse, in states of shock associated with low peripheral resistances or to restore and/or keep physiological pressure levels.

According to a further aspect a method for the treatment of cardiac circulatory collapse, especially in states of shock associated with low peripheral resistances or to restore and/or keep physiological pressure levels is provided said method comprising the administration of an effective amount of a noradrenaline injectable solution that is stable, substantially free of preservatives and/or anti-oxidizing agents, as defined in any one of appended claims 9-16.

Typically, the stable noradrenaline solution of the invention is administered by intravenous or intra-arterial injection. In certain embodiments, there is provided an infusion of a therapeutically active amount of the above stable noradrenaline solution according to the invention.

DETAILED DESCRIPTION OF THE INVENTION

The Applicant has identified a process for producing noradrenaline injectable solutions, in particular at low concentrations, which are particularly stable in the absence of anti-oxidizing, preservative and/or complexing agents.

According to certain aspects the invention thus relates to a process for the production of a noradrenaline injectable solution, in particular with a content of noradrenaline of 0.04 to 0.20 mg/ml comprising the following steps:

a. dissolving noradrenaline and optionally an excipient in deoxygenated or degassed water to give a noradrenaline solution,
b. adjusting the pH of the noradrenaline solution by adding an aqueous solution of hydrochloric acid to reach a pH from 3.2 to 3.6,
c. filtrating the noradrenaline solution resulting from step b. in a current of inert gas, typically nitrogen,
d. distributing the noradrenaline solution of step c. in a current of inert gas, typically nitrogen,
e. sterilizing the noradrenaline solution obtained by step d.

According to some embodiments of the invention, the dissolving step includes dissolving 0.04 to 0.20 mg of noradrenaline per ml of infusion water.

Typically, the water used to prepare the solution is degassed or deaerated, distilled, sterile, pyrogen-free water for pharmaceutical use.

According to some embodiments, the deoxygenated or degassed water is obtained by blowing or bubbling an inert gas current, typically based on nitrogen or a noble gas such as argon.

In the process of the invention, any inert gas can be used, such as nitrogen, argon and mixtures thereof, to remove oxygen or air in one or more of the steps and to limit risks of oxidation of the noradrenaline contained in the injectable aqueous solution.

Typically, in step a) noradrenaline and any optional excipients is dissolved in water for pharmaceutical sterile preparations, for example deaerated or degassed by bubbling or blowing an inert gas. Dissolution can be carried out within a suitable inert container, in which air or oxygen have been removed by passage of inert gas. During dissolution of the noradrenaline an inert gas can be blown into the container or tank of the solution, to remove any residual oxygen.

According to some embodiments, upon completion of process step a) the noradrenaline injectable solution obtained has a residual oxygen content equal to or lower than 100 ppb.

In process step b), the pH of the noradrenaline aqueous solution is finely adjusted within the selected range of 3.2 to 3.6, preferably within a pH range of 3.3 to 3.6, in particular until a value close to 3.4 is reached, for example, typically by adding 1N HCl, in order to further stabilize the solution, reducing noradrenaline degradation.

The Applicant has indeed verified that pH values of the solution higher than 3.6 cause an increase of the formation of arterenone, while pH values lower than 3.2 have greater incidence in the appearance of d-noradrenaline.

It was unexpectedly observed that, even a small variation or adjustment of the pH value of the noradrenaline injectable solution from 3.1 to 3.2, even more and especially from 3.1 to 3.3, causes a significant reduction or absence in the racemization of noradrenaline to d-noradrenaline and an increase to the therapeutic activity as well as stability of the injectable solution.

Therefore, the specific conditions of the process of the invention minimize the formation of arterenone, the main degradation product of noradrenaline and enantiomer of d-noradrenaline, which features lower therapeutic activity.

Step c) of filtration of the process is performed by passing the solution containing noradrenaline through a filter of the type for sterilization. Passage of the noradrenaline solution through the filter can be speeded up by blowing a current of inert gas which acts as a carrier.

Suitable filters are those used in the pharmaceutical technology for preparation of sterile injectable solutions.

In step d), the noradrenaline solution is distributed in suitable containers such vials or ampoules depyrogenated preferably in the presence of inert gas, typically nitrogen, in order to minimize the volume of residual oxygen in the head of the sealed bottle and to prevent oxidative effects that may affect the stability of the solution itself.

Carrying out both steps c) and d), respectively for filtration and filling in nitrogen current, fulfils the main purpose of keeping the values of residual oxygen in the noradrenaline injectable solution to very low levels or oxygen free.

In some embodiments, at the end of step d), the noradrenaline injectable solution obtained has a residual oxygen content equal to or lower than 100 ppb.

The diluted noradrenaline solution sterilization step may be accomplished by heating, typically at temperatures above 100° C., for a time suitable for sterilization, for example equal to or greater than 15 minutes.

Surprisingly, the noradrenaline injectable solution at low concentration was stable after sterilization for 15 minutes at 121° C.

The inventors have found that the substantial absence of air or oxygen and the correction of the pH of the solution to a value in the range of 3.2 to 3.6, in particular close to 3.4 units, increases the stability of the noradrenaline solution, allowing storage at room temperature for long periods of time, up to 6 months.

According to some aspects of the invention, the steps of the process of manufacture are carried out in sterile environments in order to avoid bacterial contamination of the noradrenaline solution.

According to a further aspect the present invention provides a noradrenaline injectable solution stable and substantially free of preservatives and/or anti-oxidizing agents, optionally containing an excipient, in which the concentration of noradrenaline is in the range of 0.04 to 0.2 mg/ml and pH is 3.2 to 3.6.

In some embodiments the noradrenaline stable injectable solution is substantially free of preservatives and/or anti-oxidizing agents and the noradrenaline concentration is between 0.04 and 0.2 mg/ml, and pH is between 3.2 and 3.6, preferably between 3.3 and 3.6.

Within the scope of the invention, by the term "substantially free of preservatives and/or anti-oxidizing agents" is meant that preservatives and/or antioxidant agents, if present, are present as impurities, typically in an amount less than 0.005% by weight, as determined by HPLC-MS.

In some embodiments the noradrenaline injectable solution is free of anti-oxidizing and/or preservative agents.

Typically, the stable, injectable solution is a water-based solution and may be obtained by a process according to any one of the embodiments previously described.

According to some embodiments, the injectable solution of the invention contains an excipient, typically NaCl, in particular at a concentration in the range of 8.2 to 8.6 mg/ml, for example equal to 8.4 mg/ml.

The injectable solution of the invention has a particularly low content of oxygen dissolved in the solvent water, typically less than 100 ppb.

According to some embodiments, the stable noradrenaline injectable solution of the invention contains less than 0.05% by weight of arterenone. According to these and other embodiments of the invention, the stable noradrenaline injectable solution of the invention has an acidic pH selected in the range of 3.2 to 3.6, preferably of 3.3 to 3.6, and may have a content of enantiomer d-noradrenaline equal to or less than 5% by weight, with respect to the total weight of active principle (noradrenaline in one of its active forms) present in the solution.

In some embodiments, the injectable solution of the invention has a pH value from 3.3 to 3.6 and a content of enantiomer d-noradrenaline equal to or less than 2% by weight or 1% by weight with respect to the total weight of noradrenaline present in the solution.

According to some embodiments, the noradrenaline contained in the injectable solution is in the form of a pharmaceutically acceptable salt, for example, bitartrate.

The noradrenaline injectable solution has a surprising stability, even at high temperatures. The inventors have conducted studies on the stability at 40° C. with the noradrenaline injectable solutions, and have found that, in these conditions of temperature, stability lasts at least 3 months.

With the present invention the inventors have achieved some significant advantages including a surprising increase of stability in injectable solutions with a concentration of 0.04 to 0.2 mg/ml and surprisingly low levels of impurities with a pH of 3.2-3.6, in particular of 3.3 to 3.6, which determine a significant increase in the product safety profile.

In addition, the low concentration noradrenaline solution is surprisingly stable at room temperature for at least 6 months.

Typically, the low concentration noradrenaline injectable solutions of the invention are filled into sterile containers such as vials or ampoules in a modified atmosphere, for example in the presence of an inert gas containing basically nitrogen and/or argon.

According to a further aspect, the present invention relates to a pharmaceutical composition comprising noradrenaline in a quantity of 0.04 to 0.2 mg/ml obtained by a process according to any one of the embodiments previously described, and a pharmaceutically acceptable carrier and/or excipient.

Pharmaceutically acceptable carriers and excipients include substances commonly used in the production techniques of pharmaceutical and medical devices.

The present invention claims the priority of the Italian patent application MI2014A000306 of 27 Feb. 2014, the content of which is entirely incorporated herein by reference.

The present invention is described below, with reference to the following examples, which are provided for illustrative purposes only and should not be understood as limiting the present invention.

Example 1

4 diluted solutions of noradrenaline at different concentration were studied:

diluted solution containing 0.04 mg/ml (2 mg/50 ml) of noradrenaline, diluted solution containing 0.06 mg/ml (3 mg/50 ml) of noradrenaline, diluted solution containing 0.12 mg/ml (6 mg/50 ml) of noradrenaline, diluted solution containing 0.20 mg/ml (10 mg/50 ml) of noradrenaline, The noradrenaline solutions were prepared using water deoxygenated by nitrification (residual oxygen <100 ppb).

The noradrenaline solutions were obtained with a process which involved the following schematic steps:

a) dissolving the active principle and the excipients in water deoxygenated by degassing in a nitrogen current b) filtrating the solution in a nitrogen current c) distribution of the solution in a nitrogen current, d) sterilizing the vials at 121° C. for 15 minutes.

After loading the blender, the water for injections was degassed by boiling and then cooled to 25° C. Sodium chloride and noradrenaline bitartrate were added in this order. The solution was kept under stirring, maintaining a constant blowing of nitrogen, for 10 minutes.

After 10 minutes, the pH value of the solution was measured and corrected with 1N hydrochloric acid, until it reached the value of 3.4 units, in any case within the range of 3.2-3.6.

| | 2 mg/50 ml | 3 mg/50 ml | 6 mg/50 ml | 10 mg/50 ml |
|---|---|---|---|---|
| pH | 3.4 | 3.5 | 3.4 | 3.5 |

The solution was filtered under nitrogen pressure in a nitrogen current and distributed in clear glass 50 ml bottles. The bottles were then subjected to terminal sterilization in autoclave under overkill conditions (121° C. for 15 minutes).

Tests carried out on the vials after sterilization gave the following results:

| | 2 mg/50 ml | 3 mg/50 ml | 6 mg/50 ml | 10 mg/50 ml |
|---|---|---|---|---|
| Color and transparency | In conformity | In conformity | In conformity | In conformity |
| pH of the solution | 3.4 | 3.5 | 3.4 | 3.5 |
| Titer of Noradrenaline (HPLC) | 99.3% | 99.2% | 98.8% | 98.7% |
| Titer of Arterenone (HPLC) | Not detected | Not detected | Not detected | <0.05% |
| Titer of impurities (HPLC) | Not detected | Not detected | <0.05% | <0.05% |

Example 2

Stability of Diluted Noradrenaline Solutions

Stability: 4 batches with concentration of noradrenaline respectively of 0.04 mg/ml, 0.06 mg/ml, 0.12 mg/ml, 0.20 mg/ml were placed at 25° C. and 40° C.

After 6 months at 25° C. and 3 months at 40° C., the solutions were unchanged from a physico-chemical point of view.

The titer of noradrenaline remains above 90%. Arterenone impurity was always below 0.2% and the total of other impurities was less than 0.5%. The enantiomer concentration remains always lower than 10%.

Example 3

Low Concentration Noradrenaline Injectable Solutions

| Noradrenaline 0.04 mg/ml | Pro 1 ml | Pro 50 ml |
|---|---|---|
| Noradrenaline Bitartrate | 0.08* mg | 4.00* mg |
| Sodium Chloride | 8.4 mg | 420.0 mg |
| Hydrochloric acid | q.s. ad pH 3.3-3.6 | q.s. ad pH 3.3-3.6 |
| Water for injections | ad 1 ml | ad 50 ml |

*Corresponding respectively to 0.04 mg and 2.00 mg of noradrenaline base

Example 4

Low Concentration Noradrenaline Injectable Solutions

| Noradrenaline 0.06 mg/ml | Pro 1 ml | Pro 50 ml |
|---|---|---|
| Noradrenaline Bitartrate | 0.12* mg | 6.00* mg |
| Sodium Chloride | 8.4 mg | 420.0 mg |
| Hydrochloric acid | q.s. ad pH 3.2-3.6 | q.s. ad pH 3.2-3.6 |
| Water for injections | ad 1 ml | ad 50 ml |

*Corresponding respectively to 0.06 mg and 3.00 mg of noradrenaline base

Example 5

Low Concentration Noradrenaline Injectable Solutions

| Noradrenaline 0.12 mg/ml | Pro 1 ml | Pro 50 ml |
|---|---|---|
| Noradrenaline Bitartrate | 0.24* mg | 12.00* mg |
| Sodium Chloride | 8.4 mg | 420.0 mg |
| Hydrochloric acid | q.s. ad pH 3.2-3.6 | q.s. ad pH 3.2-3.6 |
| Water for injections | ad 1 ml | ad 50 ml |

*Corresponding respectively to 0.12 mg and 6.00 mg of noradrenaline base

Example 6

Low Concentration Noradrenaline Injectable Solutions

| Noradrenaline 0.2 mg/ml | Pro 1 ml | Pro 50 ml |
|---|---|---|
| Noradrenaline Bitartrate | 0.40* mg | 20.0* mg |
| Sodium Chloride | 8.4 mg | 420.0 |
| Hydrochloric acid | q.s. ad pH 3.3-3.6 | q.s. ad pH 3.3-3.6 |
| Water for injections | ad 1 ml | ad 50 ml |

*Corresponding respectively to 0.20 mg and 10.0 mg of noradrenaline base

The invention claimed is:

1. A stable injectable noradrenaline solution comprising noradrenaline, a solvent, an excipient, and hydrochloric acid, wherein the amount of noradrenaline is from 0.04 to 0.2 mg/ml, the solvent is degassed or deaerated water, the excipient is NaCl, and the pH of the solution is in the range of from 3.3 to 3.6, and wherein the solution is free of preservatives and anti-oxidizing agents.

2. The stable injectable noradrenaline solution according to claim 1, obtained by a process comprising:

a. dissolving noradrenaline and the excipient in deoxygenated or degassed water, to obtain a concentration of noradrenaline from 0.04 to 0.20 mg/ml, b. adjusting the pH of the resulting solution by adding hydrochloric acid until a value in the range from 3.3 to 3.6 is achieved, c. filtrating the resulting noradrenaline solution in an inert gas current, d. distributing the noradrenaline solution in an inert gas current, *and* e. sterilizing the noradrenaline solution.

3. The stable injectable noradrenaline solution according to claim 1, *having an* oxygen content [is] equal to or lower than 100 ppb.

*4. A stable injectable noradrenaline solution comprising noradrenaline or a pharmaceutically acceptable salt thereof, a solvent, an excipient, and hydrochloric acid, wherein the concentration of noradrenaline or pharmaceutically acceptable salt thereof based on the weight of noradrenaline base is from 0.04 to 0.2 mg/ml, the solvent consists of degassed or deaerated water, the excipient is NaCl, and the pH of the solution is in the range of from 3.3 to 3.6, and wherein the solution is free of preservatives and anti-oxidizing agents and complexing agents.*

*5. The stable injectable noradrenaline solution according to claim 1, in one or more sealed containers, obtained by a process comprising:*

*a) dissolving noradrenaline or pharmaceutically acceptable salt thereof and the excipient in deoxygenated or degassed water, to obtain a concentration of noradrenaline or pharmaceutically acceptable salt thereof based on the weight of the noradrenaline base of from 0.04 to 0.2 mg/ml,*

*b) adjusting the pH of the resulting solution by adding hydrochloric acid until a value in the range of from 3.3 to 3.6 is achieved,*

*c) filtrating the resulting noradrenaline solution in an inert gas current,*

*d) distributing the noradrenaline solution in an inert gas current into said one or more containers, and*

*e) sterilizing the noradrenaline solution,*

*wherein said sterilizing comprises filtrating, optionally by step (c), or heat sterilizing.*

*6. The stable injectable noradrenaline solution according to claim 1, wherein the solvent has an oxygen content equal to or lower than 100 ppb.*

*7. The solution of claim 4, wherein the concentration of noradrenaline or pharmaceutically acceptable salt thereof based on the weight of noradrenaline base is from 0.04 to 0.12 mg/ml.*

*8. The solution of claim 4, wherein, after six months storage at 25° C., the solution comprises:*

*a) <0.2% arterenone;*

*b) <0.5% impurities other than arterenone; and*

*c) <10% d-noradrenaline;*

*based on the weight of the noradrenaline base.*

*9. The solution of claim 5 wherein said sterilizing comprises filtrating.*

*10. The solution of claim 5, wherein the concentration of noradrenaline or pharmaceutically acceptable salt thereof based on the weight of noradrenaline base is from 0.04 to 0.12 mg/ml.*

*11. The solution of claim 5, wherein, after six months storage at 25° C., the solution comprises:*

*a) <0.2% arterenone;*

*b) <0.5% impurities other than arterenone; and*

*c) <10% d-noradrenaline;*

*based on the weight of the noradrenaline base.*

*12. A stable injectable noradrenaline solution comprising noradrenaline or a pharmaceutically acceptable salt thereof, a solvent, an excipient, and hydrochloric acid, wherein the concentration of noradrenaline or pharmaceutically acceptable salt thereof based on the weight of noradrenaline base is about 0.04 mg/ml, the solvent consists of degassed or deaerated water, the excipient is NaCl, and the pH of the solution is in the range of from 3.3 to 3.6, and wherein the solution is free of preservatives and anti-oxidizing agents and complexing agents.*

*13. The stable injectable noradrenaline solution according to claim 12, in one or more sealed containers, obtained by a process comprising:*

*a) dissolving noradrenaline or a pharmaceutically acceptable salt thereof in deoxygenated or degassed water, to obtain a solution having a concentration of noradrenaline or pharmaceutically acceptable salt thereof based on the weight of the noradrenaline base of about 0.04 mg/ml,*

*b) adjusting the pH of the solution by adding hydrochloric acid until a value in the range of from 3.3 to 3.6 is achieved,*

*c) filtrating the solution in an inert gas current,*

*d) distributing the solution in an inert gas current into said one or more containers, and*

*e) sterilizing the solution,*

*wherein said sterilizing comprises filtrating, optionally by step (c), or heat sterilizing.*

*14. The solution of claim 12, wherein, after six months storage at 25° C., the solution comprises:*

*a) <0.2% arterenone;*

*b) <0.5% impurities other than arterenone; and*

*c) <10% d-noradrenaline;*

*based on the weight of the noradrenaline base.*

*15. The solution of claim 13, wherein said sterilizing comprises filtrating.*

*16. The solution of claim 13, wherein, after six months storage at 25° C., the solution comprises:*

*a) <0.2% arterenone;*

*b) <0.5% impurities other than arterenone; and*

*c) <10% d-noradrenaline;*

*based on the weight of the noradrenaline base.*

*17. A stable injectable noradrenaline solution comprising noradrenaline bitartrate, a solvent, an excipient, and hydrochloric acid, wherein the concentration of noradrenaline bitartrate based on the weight of noradrenaline base is from 0.04 to 0.2 mg/ml, the solvent consists of degassed or deaerated water, the excipient is NaCl, the pH of the solution is in the range of from 3.3 to 3.6, and the solution is free of preservatives and anti-oxidizing agents.*

*18. The stable injectable noradrenaline solution according to claim 17, in one or more sealed containers, obtained by a process comprising:*

*a) dissolving noradrenaline bitartrate in deoxygenated or degassed water, to obtain a solution having a concen-*

*tration of noradrenaline bitartrate based on the weight of the noradrenaline base of from 0.04 to 0.2 mg/ml,*

*b) adjusting the pH of the solution by adding hydrochloric acid until a value in the range of from 3.3 to 3.6 is achieved,*

*c) filtrating the solution in an inert gas current,*

*d) distributing the solution in an inert gas current into said one or more containers, and*

*e) sterilizing the solution,*

*wherein said sterilizing comprises filtrating, optionally by step (c), or heat sterilizing.*

*19. The solution of claim 17, wherein, after six months storage at 25° C., the solution comprises:*

*a) <0.2% arterenone;*

*b) <0.5% impurities other than arterenone; and*

*c) <10% d-noradrenaline;*

*based on the weight of the noradrenaline base.*

*20. The solution of claim 18, wherein said sterilizing comprises filtrating.*

*21. The solution of claim 18, wherein, after six months storage at 25° C., the solution comprises:*

*a) <0.2% arterenone;*

*b) <0.5% impurities other than arterenone; and*

*c) <10% d-noradrenaline;*

*based on the weight of the noradrenaline base.*

*22. A stable injectable noradrenaline solution comprising noradrenaline bitartrate, a solvent, an excipient, and hydrochloric acid, wherein the concentration of noradrenaline bitartrate based on the weight of noradrenaline base is about 0.04 mg/ml, the solvent consists of degassed or deaerated water, the excipient is NaCl, the pH of the solution is in the range of from 3.3 to 3.6, and the solution is free of preservatives and anti-oxidizing agents.*

*23. The stable injectable noradrenaline solution according to claim 22, in one or more sealed containers, obtained by a process comprising:*

*a) dissolving noradrenaline bitartrate in deoxygenated or degassed water, to obtain a solution having a concentration of noradrenaline bitartrate based on the weight of the noradrenaline base of about 0.04 mg/ml,*

*b) adjusting the pH of the solution by adding hydrochloric acid until a value in the range of from 3.3 to 3.6 is achieved,*

*c) filtrating the solution in an inert gas current,*

*d) distributing the solution in an inert gas current into said one or more containers, and*

*e) sterilizing the solution,*

*wherein said sterilizing comprises filtrating, optionally by step (c), or heat sterilizing.*

*24. The solution of claim 22, wherein, after six months storage at 25° C., the solution comprises:*

*a) <0.2% arterenone;*

*b) <0.5% impurities other than arterenone; and*

*c) <10% d-noradrenaline;*

*based on the weight of the noradrenaline base.*

*25. The solution of claim 23, wherein said sterilizing comprises filtrating.*

* * * * *